US009226859B1

(12) United States Patent
Knight (10) Patent No.: US 9,226,859 B1
(45) Date of Patent: Jan. 5, 2016

(54) PET DIAPER AND CLOTHING COMPONENT SYSTEM

(71) Applicant: Randi L. Knight, Springfield, VA (US)

(72) Inventor: Randi L. Knight, Springfield, VA (US)

(*) Notice: Subject to any disclaimer, the term of this patent is extended or adjusted under 35 U.S.C. 154(b) by 260 days.

(21) Appl. No.: 13/921,952

(22) Filed: Jun. 19, 2013

(51) Int. Cl.
*A61F 13/15* (2006.01)
*A01K 13/00* (2006.01)
*A01K 23/00* (2006.01)
*A61F 13/49* (2006.01)
*A61F 13/66* (2006.01)

(52) U.S. Cl.
CPC ......... *A61F 13/49009* (2013.01); *A01K 13/006* (2013.01); *A01K 23/00* (2013.01); *A01K 23/005* (2013.01); *A61F 13/15* (2013.01); *A61F 13/66* (2013.01); *A61F 2013/15186* (2013.01)

(58) Field of Classification Search
CPC ... A01K 23/00; A01K 23/005; A01K 13/006; A91K 13/006; A61F 2013/15186; A61F 13/15; A61F 13/49; A61F 13/66; A61F 13/68; A61F 13/70; A61F 13/72; A61F 13/74; A61F 13/76; A61F 13/78; A61F 13/80; A61F 13/82
USPC ................... 604/385.09, 393, 397, 398–402; 119/867–869, 850, 852, 854, 856; 54/79.1, 79.2, 79.3
See application file for complete search history.

(56) References Cited

U.S. PATENT DOCUMENTS

| 5,662,640 | A  | * | 9/1997  | Daniels ................. 604/392 |
| 6,557,497 | B1 | * | 5/2003  | Milligan ................ 119/850 |
| D480,842  | S  |   | 10/2003 | Grodecki |
| 6,837,191 | B2 |   | 1/2005  | Brewington |
| 8,807,090 | B1 | * | 8/2014  | Potts et al. ............ 119/850 |
| 2005/0154367 | A1 |   | 7/2005 | Ikegami |
| 2009/0173290 | A1 |   | 7/2009 | Freitag |
| 2011/0226193 | A1 | * | 9/2011 | Williams ............... 119/850 |
| 2012/0174875 | A1 | * | 7/2012 | Wetzel ................... 119/838 |

* cited by examiner

*Primary Examiner* — Lynne Anderson
*Assistant Examiner* — Bradley Philips (57) ABSTRACT

A washable pet diaper and clothing component system for preventing a pet from urinating or defecating on a ground surface features a tubular torso component with an elastic head aperture, a first elastic leg aperture, and a second elastic leg aperture. A series of male snap components is located on each of a torso component bottom and a torso component top. The system features a pelvic component with an elastic tail aperture. A series of female snap components is located on each of a pelvic component bottom and a pelvic component top. The pelvic component features a padded absorbent member centrally located in a groin region of the pelvic component.

7 Claims, 7 Drawing Sheets

FIG. 8

PET DIAPER AND CLOTHING COMPONENT SYSTEM

FIELD OF THE INVENTION

The present invention relates to pet diapers or more specifically washable pet diaper and clothing component systems.

BACKGROUND OF THE INVENTION

Pets have been enjoyed by mankind for thousands of years, however, in some cases a pet may urinate or defecate in an area that is not permissible. The present invention features a washable pet diaper and clothing component system for preventing a pet from urinating or defecating on a ground surface.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a washable pet diaper and clothing component system for preventing a pet from urinating or defecating on a ground surface. In some embodiments, the system comprises a tubular torso component. In some embodiments, an elastic head aperture is centrally located at an intersection of a torso component anterior end and a torso component top. In some embodiments, a first elastic leg aperture is located on a torso component bottom adjacent to a torso component first side close to the torso component anterior end. In some embodiments, a second elastic leg aperture is located on the torso component bottom adjacent to a torso component second side close to the torso component anterior end.

In some embodiments, a series of male snap components is located on the torso component bottom. In some embodiments, a series of male snap components is located on the torso component top. In some embodiments, the torso component is constructed from a first material.

In some embodiments, the system comprises a pelvic component. In some embodiments, an elastic tail aperture is centrally located at an intersection of a pelvic component posterior end and a pelvic component top.

In some embodiments, a pair of female snap components is located on a pelvic component bottom. In some embodiments, a pair of female snap components is located on the pelvic component top. In some embodiments, the pelvic component is constructed from a first material.

In some embodiments, the pelvic component comprises a padded absorbent member centrally located in a groin region of the pelvic component. In some embodiments, the absorbent member is located from a pelvic component anterior end running to the elastic tail aperture. In some embodiments, the absorbent member is constructed from a second material.

DESCRIPTION OF PREFERRED EMBODIMENTS

Figure 1:
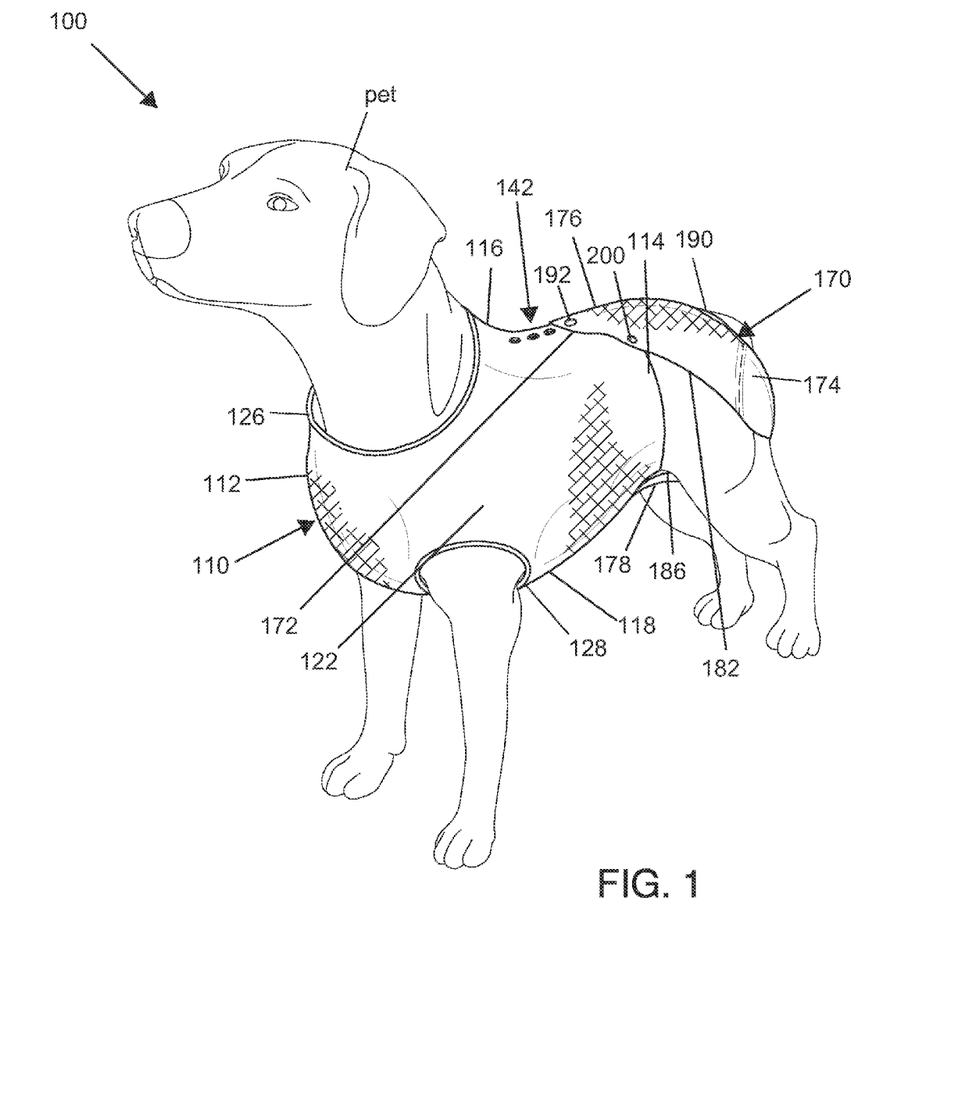
FIG. 1 shows a perspective view of the present invention.
Figure 2:
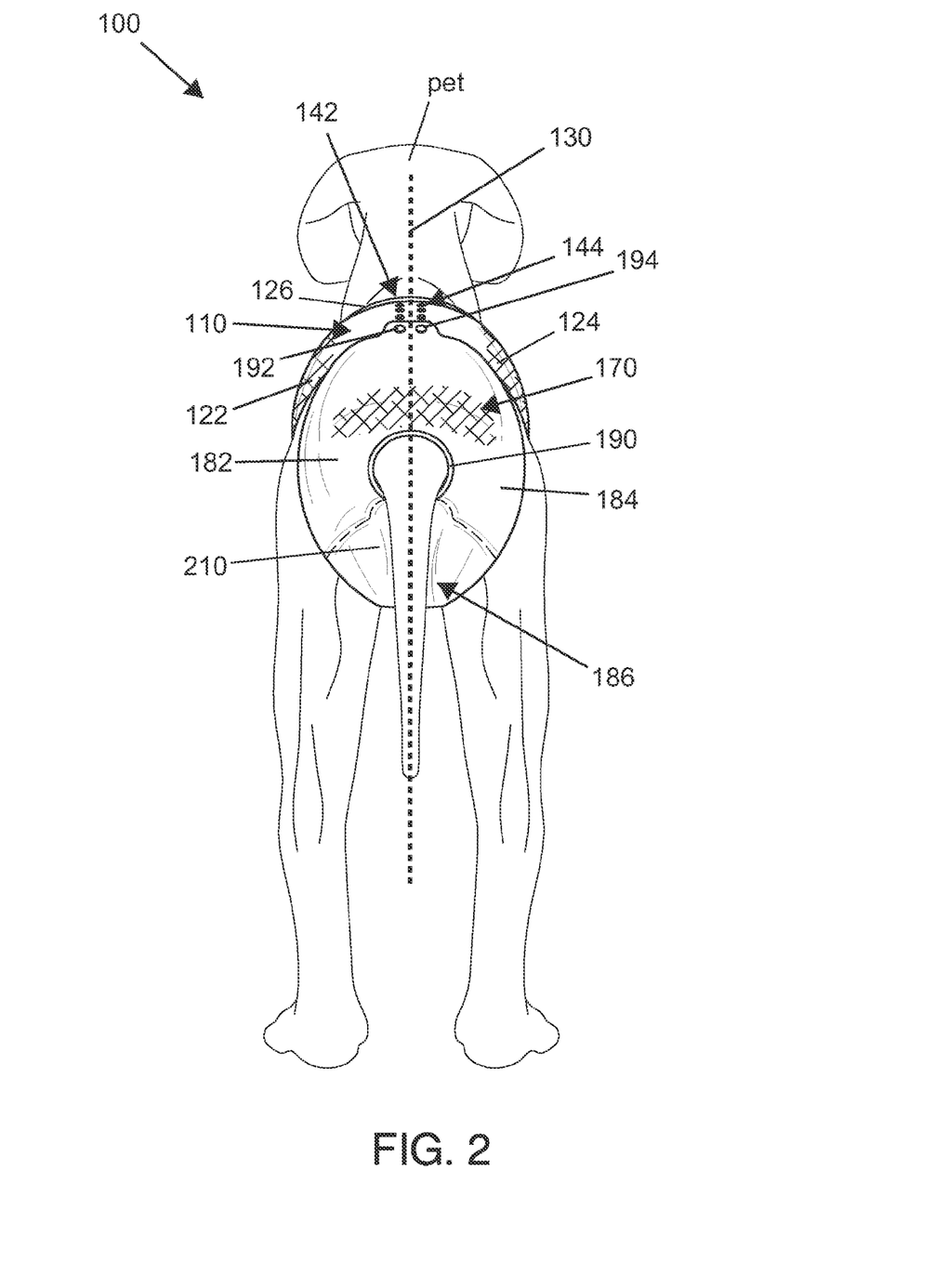
FIG. 2 shows a rear view of the present invention.
Figure 3:
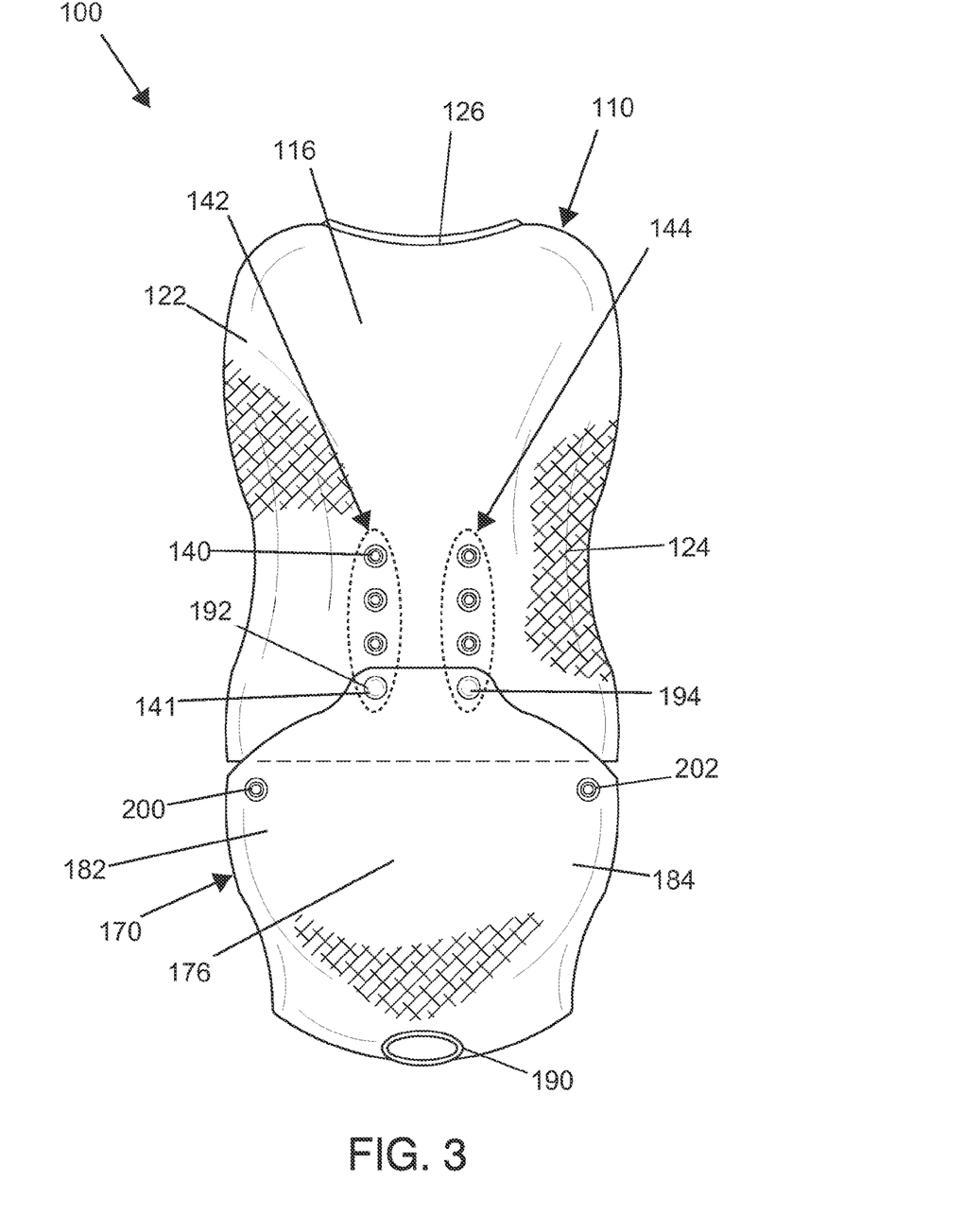
FIG. 3 shows a top view of the present invention.
Figure 4:
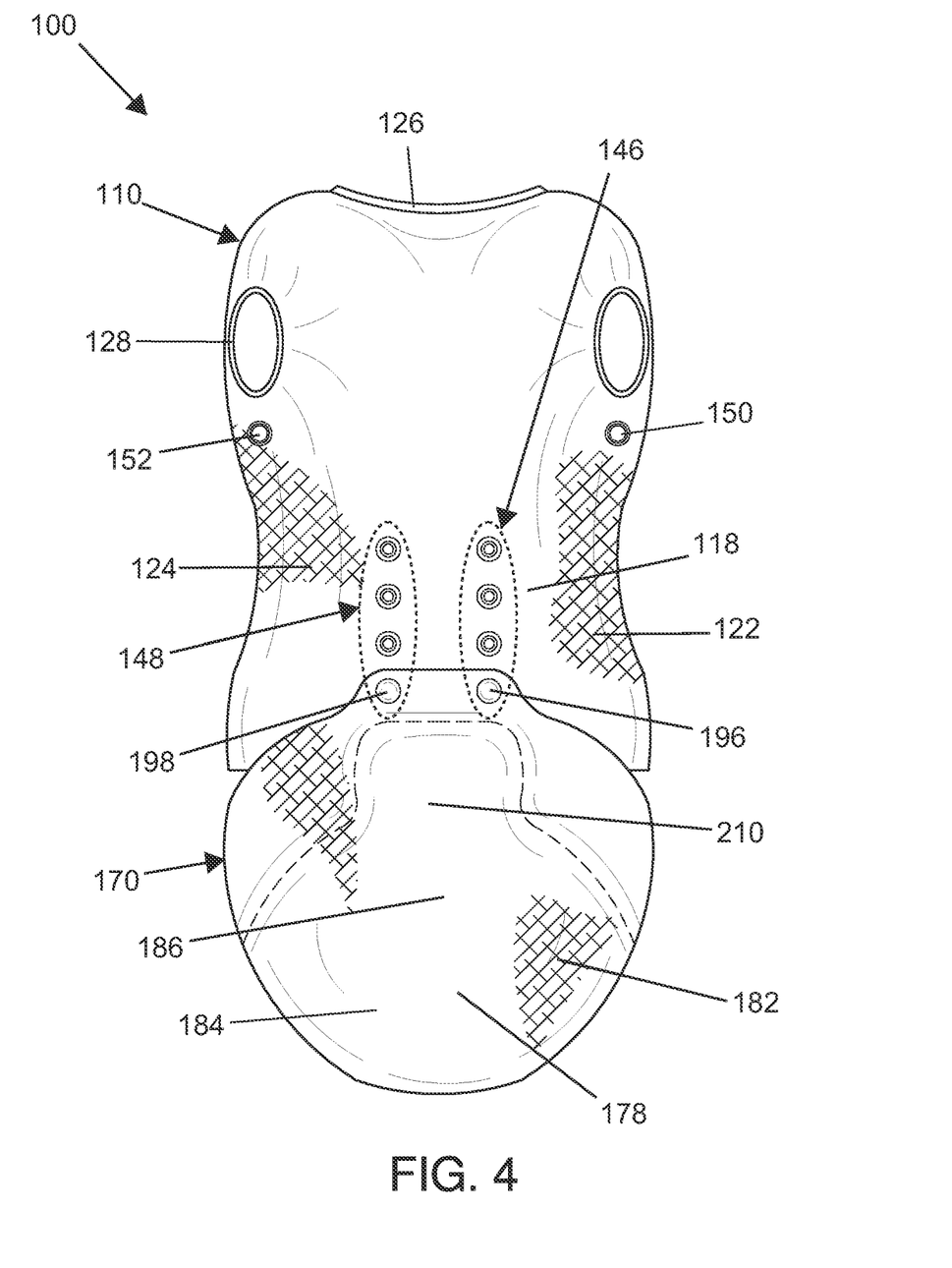
FIG. 4 shows a bottom view of the present invention.
Figures 5, 6:
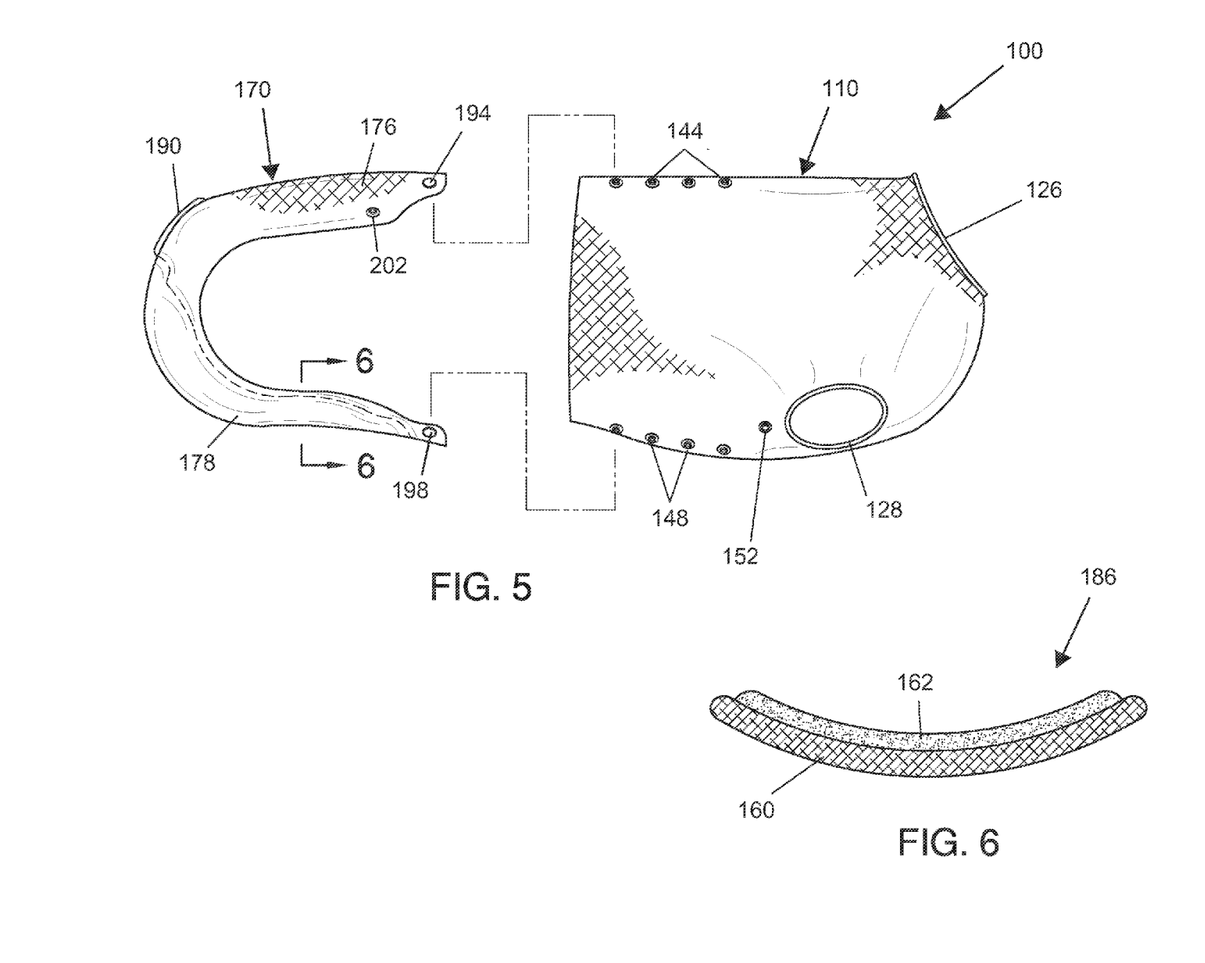
FIG. 5 shows a side view of the present invention.
FIG. 6 shows a cross-sectional view of the pelvic component groin region of the present invention.
Figure 7:
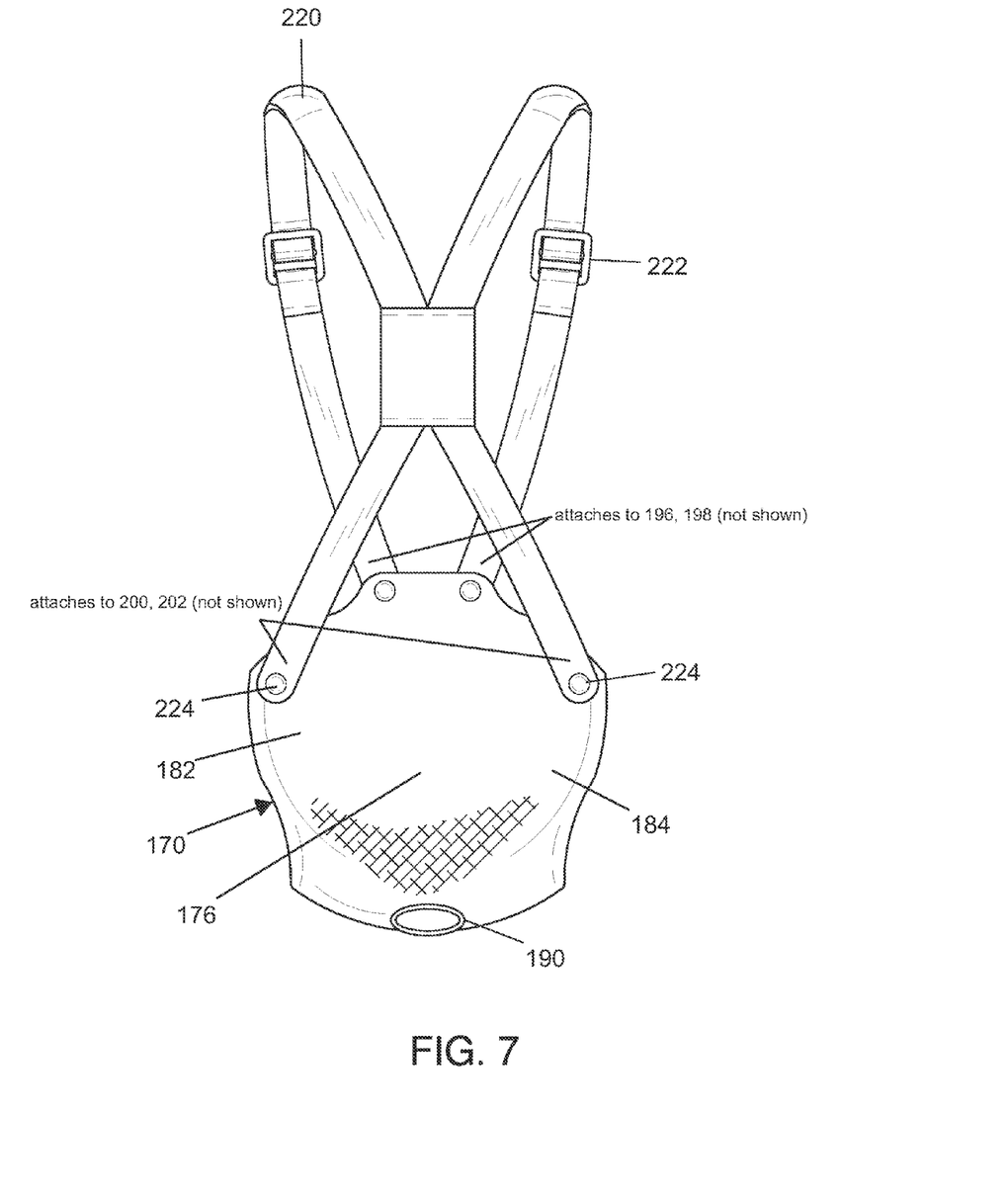
FIG. 7 shows an alternative embodiment of the present invention.
Figure 8:
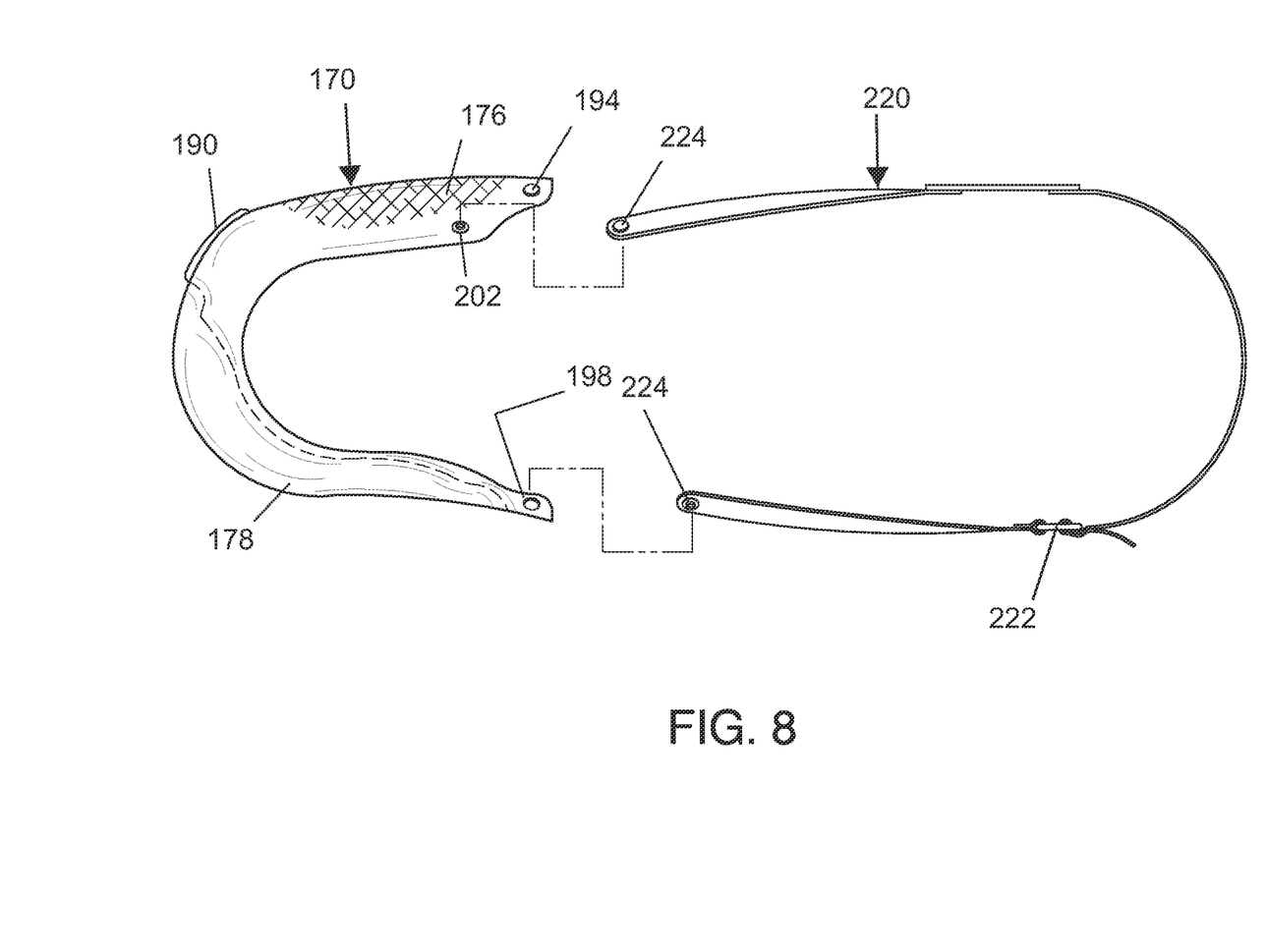
FIG. 8 shows an alternative embodiment of the present invention.

Following is a list of elements corresponding to a particular element referred to herein:
100 Pet diaper and clothing component system
110 Torso component
112 Torso component anterior end
114 Torso component posterior end
116 Torso component top
118 Torso component bottom
122 Torso component first side
124 Torso component second side
126 Head aperture
128 Leg aperture
130 Center plane
140 Male snap component
141 Female snap component
142 First series of male snap components
144 Second series of male snap components
146 Third series of male snap components
148 Fourth series of male snap components
150 First hip mating female snap component
152 Second hip mating female snap component
160 First material
162 Second material
170 Pelvic component
172 Pelvic component anterior end
174 Pelvic component posterior end
176 Pelvic component top
178 Pelvic component bottom
182 Pelvic component first side
184 Pelvic component second side
186 Pelvic component groin region
190 Tail aperture
192 First female snap component
194 Second female snap component
196 Third female snap component
198 Fourth female snap component
200 First hip male snap component
202 Second hip male snap component
210 Padded absorbent member
220 Suspenders
222 Suspender adjustment component
224 Suspender snap component Referring now to FIG. 1-8, the present invention features a washable pet diaper and clothing component system (100) for preventing a pet from urinating or defecating on a ground surface. In some embodiments, the system (100) comprises a tubular torso component (110) having a torso component anterior end (112), an open torso component posterior end (114), a torso component top (116), a torso component bottom (118), a torso component first side (122), and a torso component second side (124).

In some embodiments, an elastic head aperture (126) is centrally located at an intersection of the torso component anterior end (112) and the torso component top (116). In some embodiments, a first elastic leg aperture (128) is located on the torso component bottom (118) on or adjacent to the torso component first side (122) close to the torso component anterior end (112). In some embodiments, a second elastic leg aperture (128) is located on the torso component bottom (118) on or adjacent to the torso component second side (124) close to the torso component anterior end (112).

In some embodiments, a vertical center plane (130) divides the torso component first side (122) from the torso component second side (124) and runs from the torso component anterior end (112) to the torso component posterior end (114).

In some embodiments, a male snap component (140) is a male snap. In some embodiments, a female snap component (141) is a female snap that mates to the male snap component (140).

In some embodiments, a first series of male snap components (142) is located on the torso component top (116) on the torso component first side (122). In some embodiments, a second series of male snap components (144) is located on the torso component top (116) on the torso component second side (124). In some embodiments, a third series of male snap components (146) is located on the torso component bottom (118) on the torso component first side (122). In some embodiments, a fourth series of male snap components (148) is located on the torso component bottom (118) on the torso component second side (124). In some embodiments, the male snap components (140) in the series provide for adjustment and fit for the system (100).

In some embodiments, a first hip mating female snap component (150) is located on the torso component bottom (118) on the torso component first side (122) posterior to the first elastic leg aperture (128). In some embodiments, a second hip mating female snap component (152) is located on the torso component bottom (118) on the torso component second side (124) posterior to the second elastic leg aperture (128). In some embodiments, the torso component (110) is constructed from a first material (160). In some embodiments, the first hip mating female snap component (150) and the second hip mating female snap component (152) are female snap components (141).

In some embodiments, the system (100) comprises a pelvic component (170) having an open pelvic component anterior end (172), a pelvic component posterior end (174), a pelvic component top (176), a pelvic component bottom (178), a pelvic component first side (182), and a pelvic component second side (184). In some embodiments, an elastic tail aperture (190) is centrally located at an intersection of the pelvic posterior end and the pelvic component top (176).

In some embodiments, a vertical center plane (130) divides the pelvic component first side (182) from the pelvic component second side (184) and runs from the pelvic component anterior end (172) to the pelvic component posterior end (174).

In some embodiments, a first female snap component (192) is located on the pelvic component top (176) on the pelvic component first side (182). In some embodiments, a second female snap component (194) is located on the pelvic component top (176) on the pelvic component second side (184). In some embodiments, a third female snap component (196) is located on the pelvic component bottom (178) on the pelvic component first side (182). In some embodiments, a fourth female snap component (198) is located on the pelvic component bottom (178) on the pelvic component second side (184).

In some embodiments, a first hip male snap component (200) is located on the pelvic component top (176) on the pelvic component first side (182). In some embodiments, a second hip male snap component (202) is located on the pelvic component top (176) on the pelvic component second side (184). In some embodiments, the pelvic component (170) is constructed from a first material (160).

In some embodiments, the first hip male snap component (200) and the second hip male snap component (202) are male snap components (140).

In some embodiments, the pelvic component (170) comprises a padded absorbent member (210) centrally located in a pelvic component groin region (186).

In some embodiments, the padded absorbent member (210) is located from the pelvic component anterior end (172) to the elastic tail aperture (190). In some embodiments, the padded absorbent member (210) is constructed from a second material (162). In some embodiments, the padded absorbent member (210) stretches between the leg openings. In some embodiments, the padded absorbent member (210) is designed to absorb urine from the pet.

In some embodiments, the tubular torso component (110) is placed on the pet via sliding the elastic head aperture (126) over a head of the pet, sliding the first elastic leg aperture (128) over a first front leg, and sliding the second elastic leg aperture (128) over a second front leg.

In some embodiments, the pelvic component (170) is placed on the pet via sliding the elastic tail aperture (190) over a tail of the pet, snapping the first female snap component (192) onto one of the first series of male snap components (142), snapping the second female snap component (194) onto one of the second series of male snap components (144), snapping the third female snap component (196) onto one of the third series of male snap components (146), snapping the fourth female snap component (198) onto one of the fourth series of male snap components (148). In some embodiments, the padded absorbent member (210) is located adjacent to the groin region of the pet.

In some embodiments, for wearing the pelvic component (170) in an alternate fashion away from the groin region of the pet for stowage allowing the groin area of the pet to be exposed, the pelvic component (170) is placed on the pet snapping the third female snap component (196) onto one of the third series of male snap components (146), snapping the fourth female snap component (198) onto one of the fourth series of male snap components (148), snapping the first hip mating female snap component (150) to the first hip male snap component (200), snapping the second hip mating female snap component (152) to the second hip male snap component (202) while tightly folding at the pelvic component groin region (186) in half.

In some embodiments, the first material (160) is a terry cloth. In some embodiments, the first material (160) is cloth. In some embodiments, the first material (160) is a breathable polyethylene film or a nonwoven and film composite.

In some embodiments, the second material (162) is terry cloth. In some embodiments, the second material (162) is cloth. In some embodiments, the second material (162) is a mixture of air-laid paper and superabsorbent polymers. In some embodiments, the second material (162) is constructed from a paper absorbent material.

In some embodiments, the system (100) is constructed from a washable material.

In some embodiments, the pelvic component (170) is disposable. In some embodiments, the pelvic component (170) is constructed from a paper material.

In some embodiments, the system (100) comprises suspenders (220). In some embodiments, the suspenders are attached to the pelvic component (170) for wearing the pelvic component (170) in an alternate fashion without the torso component (110). In some embodiments, the suspenders (220) are adjustable via one or more suspender adjustment components (222) located on the suspenders (220). In some embodiments, the suspenders (220) comprise two suspender adjustment components (222). In some embodiments, the suspenders attach to the pelvic component (170) via a plurality of suspender snap components (224). In some embodiments, the plurality of suspender snap components (224) is attached to each of the third female snap component (196), fourth female snap component (198), the first hip male snap component (200), and the second hip male snap component (202). In some embodiments, the suspender snap component (224) is either a male snap or a female snap based on where it is designed to attach.

In some embodiments, the suspenders (220) are used in lieu of the torso component (110).

As used herein, the term "about" refers to plus or minus 10% of the referenced number.

The disclosures of the following U.S. Patents are incorporated in their entirety by reference herein: U.S. Pat. No. D 480,842; U.S. Patent Pub. No. 2009/0173290; U.S. Patent Pub. No. 2005/0154367; U.S. Pat. No. 6,837,191; U.S. Pat. No. 6,557,497; and U.S. Pat. No. 5,662,640.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A washable pet diaper and clothing component system (100) for preventing a pet from urinating or defecating on a ground surface, wherein the system (100) comprises:
   (a) a tubular torso component (110) having a torso component anterior end (112), an open torso component posterior end (114), a torso component top (116), a torso component bottom (118), a torso component first side (122), and a torso component second side (124),
   wherein an elastic head aperture (126) is centrally disposed at an intersection of the torso component anterior end (112) and the torso component top (116),
   wherein a first elastic leg aperture (128) is disposed on the torso component bottom (118) adjacent to the torso component first side (122) proximal to the torso component anterior end (112), wherein a second elastic leg aperture (128) is disposed on the torso component bottom (118) adjacent to the torso component second side (124) proximal to the torso component anterior end (112),
   wherein a vertical center plane (130) divides the torso component first side (122) from the torso component second side (124) and runs from the torso component anterior end (112) to the torso component posterior end (114),
   wherein a first series of male snap components (142) is disposed on the torso component top (116) on the torso component first side (122), wherein a second series of male snap components (144) is disposed on the torso component top (116) on the torso component second side (124), wherein a third series of male snap components (146) is disposed on the torso component bottom (118) on the torso component first side (122),
   wherein a fourth series of male snap components (148) is disposed on the torso component bottom (118) on the torso component second side (124),
   wherein a first hip mating female snap component (150) is disposed on the torso component bottom (118) on the torso component first side (122) posterior to the first elastic leg aperture (128), wherein a second hip mating female snap component (152) is disposed on the torso component bottom (118) on the torso component second side (124) posterior to the second elastic leg aperture (128),
   wherein the torso component (110) is constructed from a first material (160); and
   (b) a pelvic component (170) having an open pelvic component anterior end (172), a pelvic component posterior end (174), a pelvic component top (176), a pelvic component bottom (178), a pelvic component first side (182), and a pelvic component second side (184),
   wherein an elastic tail aperture (190) is centrally disposed at an intersection of the pelvic component posterior end (174) and the pelvic component top (176),
   wherein the vertical center plane (130) divides the pelvic component first side (182) from the pelvic component second side (184) and runs from the pelvic component anterior end (172) to the pelvic component posterior end (174),
   wherein a first female snap component (192) is disposed on the pelvic component top (176) on the pelvic component first side (182), wherein a second female snap component (194) is disposed on the pelvic component top (176) on the pelvic component second side (184), wherein a third female snap component (196) is disposed on the pelvic component bottom (178) on the pelvic component first side (182), wherein a fourth female snap component (198) is disposed on the pelvic component bottom (178) on the pelvic component second side (184),
   wherein a first hip male snap component (200) is disposed on the pelvic component top (176) on the pelvic component first side (182), wherein a second hip male snap component (202) is disposed on the pelvic component top (176) on the pelvic component second side (184),
   wherein the pelvic component (170) is constructed from the first material (160),
   wherein the pelvic component (170) comprises a padded absorbent member (210) centrally disposed in a pelvic component groin region (186), wherein the padded absorbent member (210) is disposed from the pelvic component anterior end (172) running to the elastic tail aperture (190), wherein the padded absorbent member (210) is constructed from a second material (162);
   wherein the tubular torso component (110) is adapted to be disposed on the pet via sliding the elastic head aperture (126) over a head of the pet, sliding the first elastic leg aperture (128) over a first front leg, and sliding the second elastic leg aperture (128) over a second front leg, wherein the pelvic component (170) is adapted to be placed on the pet via sliding the elastic tail aperture (190) over a tail of the pet, snapping the first female snap component (192) onto one of the first series of male snap components (142), snapping the second female snap component (194) onto one of the second series of male snap components (144), snapping the third female snap component (196) onto one of the third series of male snap components (146), snapping the fourth female snap component (198) onto one of the fourth series of male snap components (148), wherein the padded absorbent member (210) is adapted to be disposed adjacent to the groin region of the pet, wherein for wearing the pelvic component (170) in an alternate fashion away from the groin region for stowage allowing the groin area of the pet to be exposed, the pelvic component (170) is adapted to be placed on the pet snapping the third female snap component (196) onto one of the third series of male snap components (146), snapping the fourth female snap component (198) onto one of the fourth series of male snap components (148), snapping the first hip mating female snap component (150) to the first hip male snap component (200), snapping the second hip mating female snap component (152) to the second hip male snap component (202) while tightly folding at the pelvic component groin region (186) in half.

2. The system (100) of claim 1, wherein the first material (160) is a terry cloth.

3. The system (100) of claim 1, wherein the second material (162) is terry cloth.

4. The system (100) of claim 1, wherein the second material (162) is constructed from a paper absorbent material.

5. The system (100) of claim 1, wherein the system (100) is constructed from a washable material.

6. The system (100) of claim 1, wherein the pelvic component (170) is disposable, wherein the pelvic component (170) is constructed from a paper material.

7. The system (100) of claim 1, wherein the system (100) comprises suspenders (220), wherein the suspenders are attached to the pelvic component (170) for wearing the pelvic component (170) in an alternate fashion without the torso component (110), wherein the suspenders (220) are adjustable via one or more suspender adjustment components (222) disposed on the suspenders (220), wherein the suspenders attach to the pelvic component (170) via a plurality of suspender snap components (224), wherein the plurality of suspender snap components (224) is attached to each of the third female snap component (196), fourth female snap component (198), the first hip male snap component (200), and the second hip male snap component (202).

\* \* \* \* \*